(12) United States Patent  
Eisinger et al.

(10) Patent No.: US 11,883,051 B2
(45) Date of Patent: Jan. 30, 2024

(54) HOLLOW GRASPERS

(71) Applicant: Covidien LP, Mansfield, MA (US)

(72) Inventors: Joseph T. Eisinger, Northford, CT (US); Justin Williams, Southbury, CT (US)

(73) Assignee: COVIDIEN LP, Mansfield, MA (US)

( * ) Notice: Subject to any disclaimer, the term of this patent is extended or adjusted under 35 U.S.C. 154(b) by 154 days.

(21) Appl. No.: 17/364,948

(22) Filed: Jul. 1, 2021

(65) Prior Publication Data

US 2022/0054157 A1    Feb. 24, 2022

Related U.S. Application Data

(60) Provisional application No. 63/069,342, filed on Aug. 24, 2020.

(51) Int. Cl.
| A61B 17/20 | (2006.01) |
| A61B 17/00 | (2006.01) |
| A61B 17/29 | (2006.01) |

(52) U.S. Cl.
CPC ...... *A61B 17/2909* (2013.01); *A61B 2017/00862* (2013.01); *A61B 2017/2902* (2013.01); *A61B 2017/2936* (2013.01); *A61B 2017/2947* (2013.01)

(58) Field of Classification Search
CPC .... A61B 2017/2939; A61B 2017/2932; A61B 2017/2901; A61B 2017/2926; A61B 2017/2936; A61B 2017/2933; A61B 2017/2947; A61B 18/1447

See application file for complete search history.

(56) References Cited

U.S. PATENT DOCUMENTS

| 5,466,243 A | 11/1995 | Schmieding et al. |
| 5,797,939 A | 8/1998 | Yoon |
| 6,632,182 B1 | 10/2003 | Treat |
| 8,986,326 B2 | 3/2015 | Satake et al. |
| 9,492,163 B2 | 11/2016 | Bagaoisan et al. |
| 9,737,320 B2 | 8/2017 | Stopek et al. |
| 10,639,025 B2 | 5/2020 | Raybin et al. |
| 2011/0060188 A1 | 3/2011 | Sharon et al. |
| 2013/0296848 A1* | 11/2013 | Allen, IV ........... A61B 18/1445 606/41 |
| 2017/0056037 A1* | 3/2017 | Kendrick ........... A61B 18/1445 |
| 2020/0146748 A1* | 5/2020 | Kase ............... A61B 17/320092 |

FOREIGN PATENT DOCUMENTS

| WO | 9509566 A1 | 4/1995 |
| WO | 2014018344 A1 | 1/2014 |

* cited by examiner

*Primary Examiner* — Majid Jamialahmadi
(74) *Attorney, Agent, or Firm* — Carter, DeLuca & Farrell LLP (57) ABSTRACT

A surgical grasper includes jaws that are transitionable between spaced apart and approximated configurations. In particular, the surgical grasper defines an unobstructed lumen for passage of a surgical instrument therethrough.

20 Claims, 10 Drawing Sheets

HOLLOW GRASPERS

CROSS-REFERENCE TO RELATED APPLICATIONS

This application claims the benefit of and priority to U.S. Provisional Patent Application No. 63/069,342, filed Aug. 24, 2020, the entire contents of which is incorporated by reference herein.

TECHNICAL FIELD

The disclosure relates to surgical devices for performing endoscopic surgical procedures. More specifically, the disclosure relates to a surgical grasper having a passage to receive a surgical instrument therethrough.

BACKGROUND

In minimally invasive surgery, the surgical procedure is performed by access to the surgical site through one or more small incisions. The surgical site is visualized by an endoscope inserted through one of the incisions and various surgical devices are inserted through the incisions to manipulate the tissue as desired. The advantages of minimally invasive surgery are well established which include reduced trauma to tissue, reduced chance of infection, faster patient recovery time, and lower hospital costs.

Minimally invasive surgical procedures typically require the tissue to be grasped and held or manipulated. It would be advantageous to provide a tissue grasper that enables use with other surgical instruments while reducing invasiveness by reducing the number of incisions during a surgical procedure.

SUMMARY

In accordance with this disclosure, a surgical grasper includes a handle assembly, an inner shaft assembly, an outer shaft, and a grasper assembly. The handle assembly includes first and second handles. The inner shaft assembly includes an inner shaft defining a lumen for passage of a surgical instrument therethrough and an engaging portion peripherally arranged with a distal portion of the inner shaft such that the engaging portion conforms to a contour of the inner shaft. A proximal portion of the inner shaft is pivotably coupled to the first handle. The outer shaft is slidably disposed about the inner shaft. The outer shaft includes a proximal portion fixedly secured to the second handle, and a distal portion including supporting fingers. The grasper assembly is operatively coupled to the supporting fingers of the outer shaft. The grasper assembly includes jaws. Each jaw includes a grasping portion and an extension member extending proximally from the grasping portion such that the extension member selectively engages the engaging portion of the inner shaft assembly. Axial displacement of the inner shaft transitions the grasper assembly between approximated and spaced apart configurations.

In an aspect, when the inner shaft is in a distal-most position, the engaging portion of the inner shaft assembly may engage central portions of the extension members of the grasper assembly to transition the grasper assembly to the spaced apart configuration.

In another aspect, when the inner shaft is in a proximal-most position, the engaging portion of the inner shaft assembly may engage proximal end portions of the extension members of the grasper assembly to transition the grasper assembly to the approximated configuration.

In yet another aspect, the supporting fingers of the outer shaft may extend distally from an outer surface of the outer shaft.

In still yet another aspect, the supporting fingers may define bores.

In still yet another aspect, each extension member of the jaws may define a bore dimensioned to receive a pin extending through a corresponding bore of the supporting finger.

In an aspect, at least one of the extension members of the jaws may define an acute angle with respect to a longitudinal axis defined by the corresponding grasping portion of the grasper assembly.

In yet another aspect, the engaging portion of the inner shaft assembly may include teeth to engage the extension members.

In still yet another aspect, the first and second handles of the handle assembly may be biased away from each other.

In still yet another aspect, the first handle may be axially movable relative to the second handle.

In an aspect, each jaw may include a pair of extension members defining a gap therebetween.

In another aspect, the gap defined by the pair of extension members may be substantially identical to a diameter of the lumen defined by the inner shaft.

In accordance with another aspect of the disclosure, a surgical grasper includes an inner shaft defining a lumen for passage of a surgical instrument therethrough, an outer shaft slidably disposed about the inner shaft, first and second jaws pivotably coupled to each other, and a pair of connectors connecting the first and second jaws to the outer shaft. The inner shaft is coupled to the first and second jaws such that when the inner shaft is in a proximal-most position, the pair of connectors is deflected radially inwards such that the first and second jaws are spaced apart, and when the inner shaft is in a distal-most position, the pair of connectors is deflected radially outwards such that the first and second jaws are approximated. The outer shaft and the grasper assembly are formed from a single tubular member.

In an aspect, the grasper assembly and the outer shaft may define axial slots adjacent each connector to enable flexing of the connector.

In another aspect, the first and second jaws may be identical.

In yet another aspect, the first jaw may include an arcuate portion and a recess opposing the arcuate portion. The arcuate portion may have a shape complementary to a shape of the recess.

In accordance with yet another aspect of the disclosure, a surgical grasper includes an inner shaft assembly, an outer shaft, and a grasper assembly. The inner shaft assembly includes an inner shaft defining a lumen for passage of a surgical instrument therethrough and an engaging portion peripherally arranged with the inner shaft such that the engaging portion conforms to a contour of the inner shaft. The outer shaft is slidably disposed about the inner shaft. The outer shaft includes opposing supporting fingers. The grasper assembly is operatively coupled to the opposing supporting fingers of the outer shaft. The grasper assembly includes opposing jaws. Each jaw includes a grasping portion and an extension member extending proximally from the grasping portion such that the extension member selectively engages the inner shaft. Axial displacement of the inner shaft transitions the grasper assembly between approximated and spaced apart configurations.

In an aspect, the outer shaft may define a lumen to receive the inner shaft therethrough.

In another aspect, the lumen of the inner shaft may have a uniform diameter.

In yet another aspect, each extension member may have a thickness smaller than or equal to a thickness of the outer shaft.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

DETAILED DESCRIPTION

The surgical grasper disclosed herein is described in detail with reference to the drawings, in which like reference numerals designate identical or corresponding elements in each of the several views.

As used herein, the term "distal" refers to the portion that is being described which is farther from a user, while the term "proximal" refers to the portion that is being described which is closer to a user. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 1:
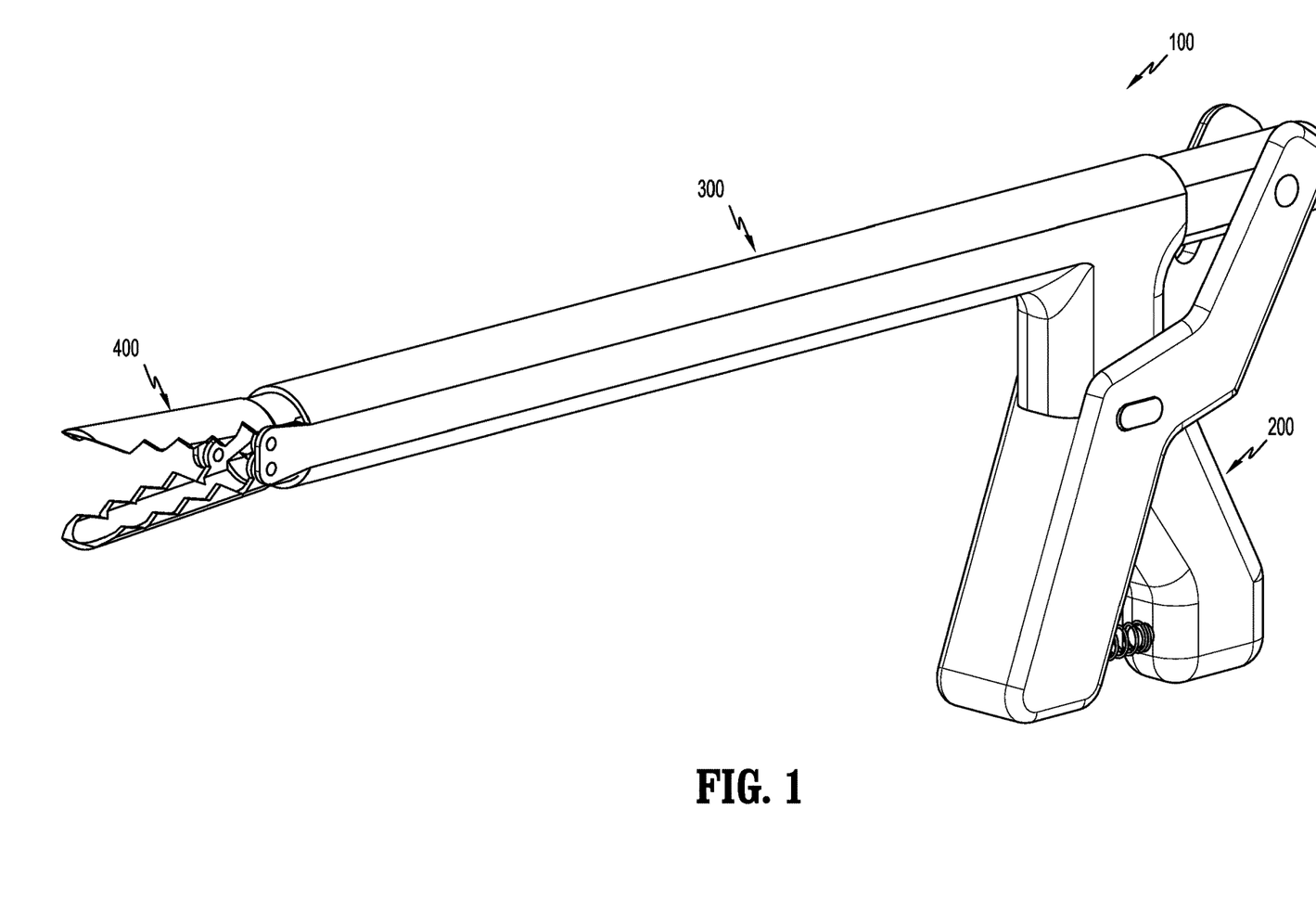
FIG. 1 is a perspective view of a surgical grasper in accordance with the disclosure.

In FIG. 1, an exemplary surgical grasper in accordance with the disclosure is shown generally as a surgical grasper 100. The surgical grasper 100 enables use with other surgical instruments, while minimizing invasiveness thereof. In particular, the surgical grasper 100 enables passage of the surgical instruments through the surgical grasper 100, as will be described below. The surgical grasper 100 may be configured as a single-use device that is discarded after use or sent to a manufacturer for reprocessing, a reusable device capable of being cleaned and/or sterilized for repeated use by the end-user, or a partially-single-use, partially-reusable device.

Figure 2:
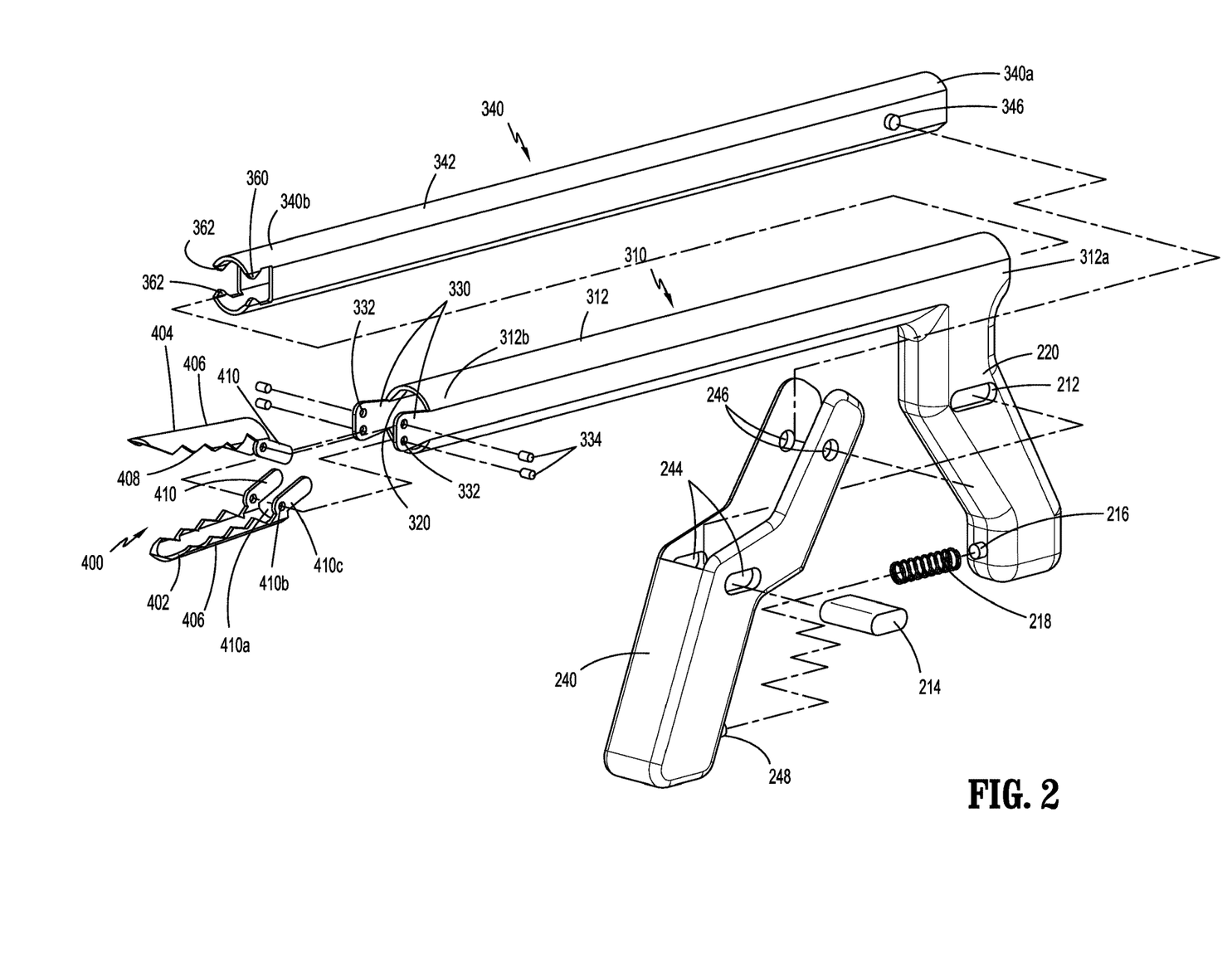
FIG. 2 is an exploded perspective view of the surgical grasper of FIG. 1 with parts separated.
Figure 3:
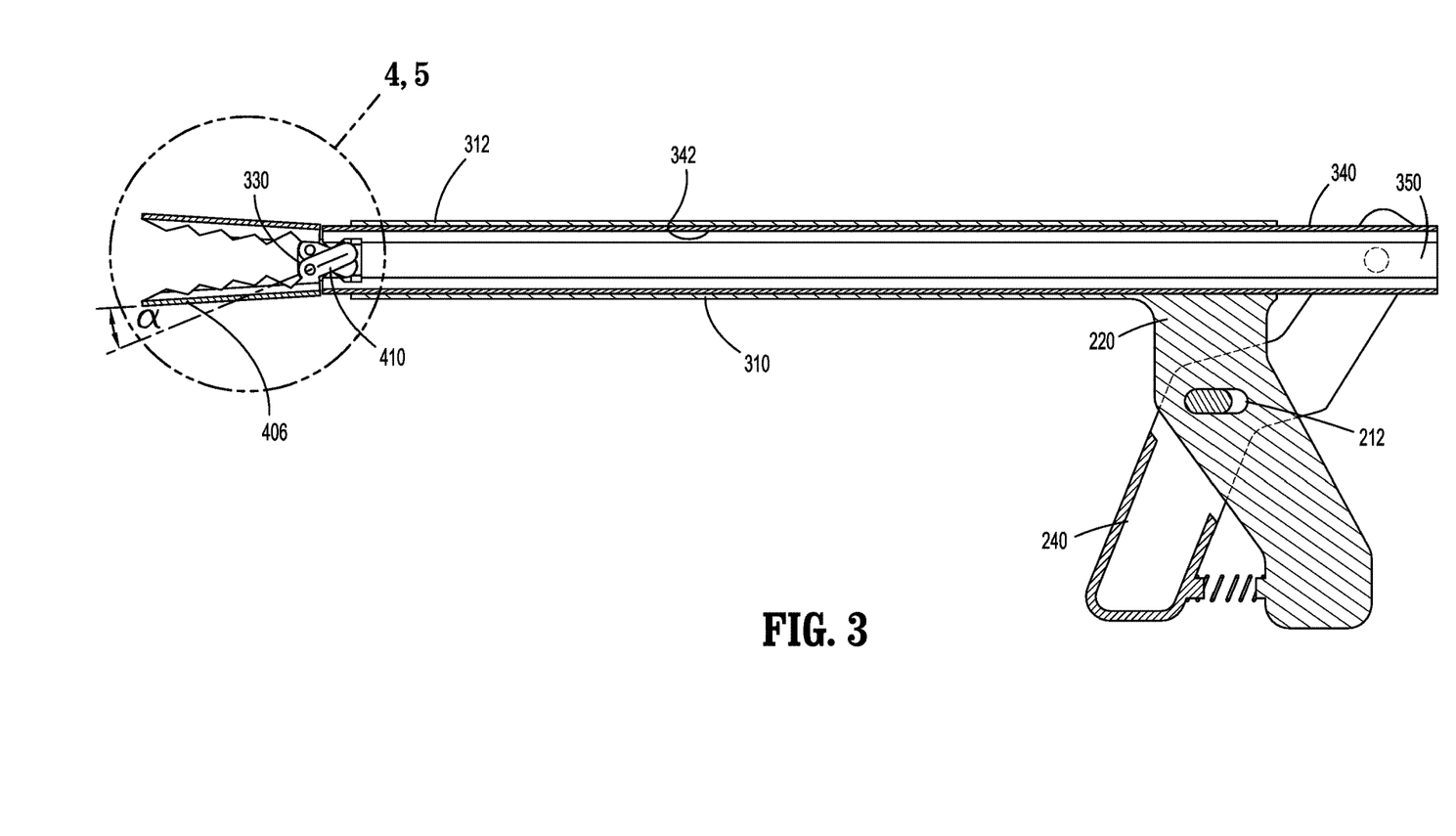
FIG. 3 is a side cross-sectional view of the surgical grasper of FIG. 1.

FIGS. 1-3 illustrate the surgical grasper 100 including a handle assembly 200, an elongate shaft assembly 300, and a grasper assembly 400 operatively coupled to the handle assembly 200. The handle assembly 200 actuates the grasper assembly 400 to transition between spaced apart and approximated configurations, as will be discussed. The elongate shaft assembly 300 includes an outer shaft assembly 310 and an inner shaft assembly 340 operatively coupled to the outer shaft assembly 310. The outer shaft assembly 310 includes an outer shaft 312 and supporting fingers 330 mounted at a distal portion 312b of the outer shaft 312. The supporting fingers 330 are peripherally arranged with the outer shaft 312. For example, the supporting fingers 330 may extend distally from an outer surface of the outer shaft 312. The outer shaft 312 defines a first lumen 320 extending therethrough. The first lumen 320 may have a uniform diameter. The first lumen 320 is dimensioned to receive an inner shaft 342 of the inner shaft assembly 340. A first handle 220 of the handle assembly 200 is securely fixed to a proximal portion 312a of the outer shaft 312.

The first handle 220 defines a camming slot 212 configured to receive a camming pin 214, as will be described below. The first handle 220 further includes a boss 216 to support a spring 218 thereon which is configured to bias a second handle 240 of the handle assembly 200 away from the first handle 220 to place the grasper assembly 400 in the spaced apart configuration, as will be discussed below. The supporting fingers 330 of the outer shaft assembly 310 operatively support the grasper assembly 400 thereon. In particular, the supporting fingers 330 extend distally from the distal portion 312b of the outer shaft 312. In particular, the supporting fingers 330 are peripherally arranged to maximize the space provided by the first lumen 320. For example, the supporting fingers 330 may extend from an outer surface of the outer shaft 312 to further maximize the space provided by the first lumen 320. In this manner, the first lumen 320 may be unobstructed and may have a uniform diameter. The supporting fingers 330 may diametrically oppose each other. Each supporting finger 330 defines bores 332 to receive respective support pins 334.

Figure 6:
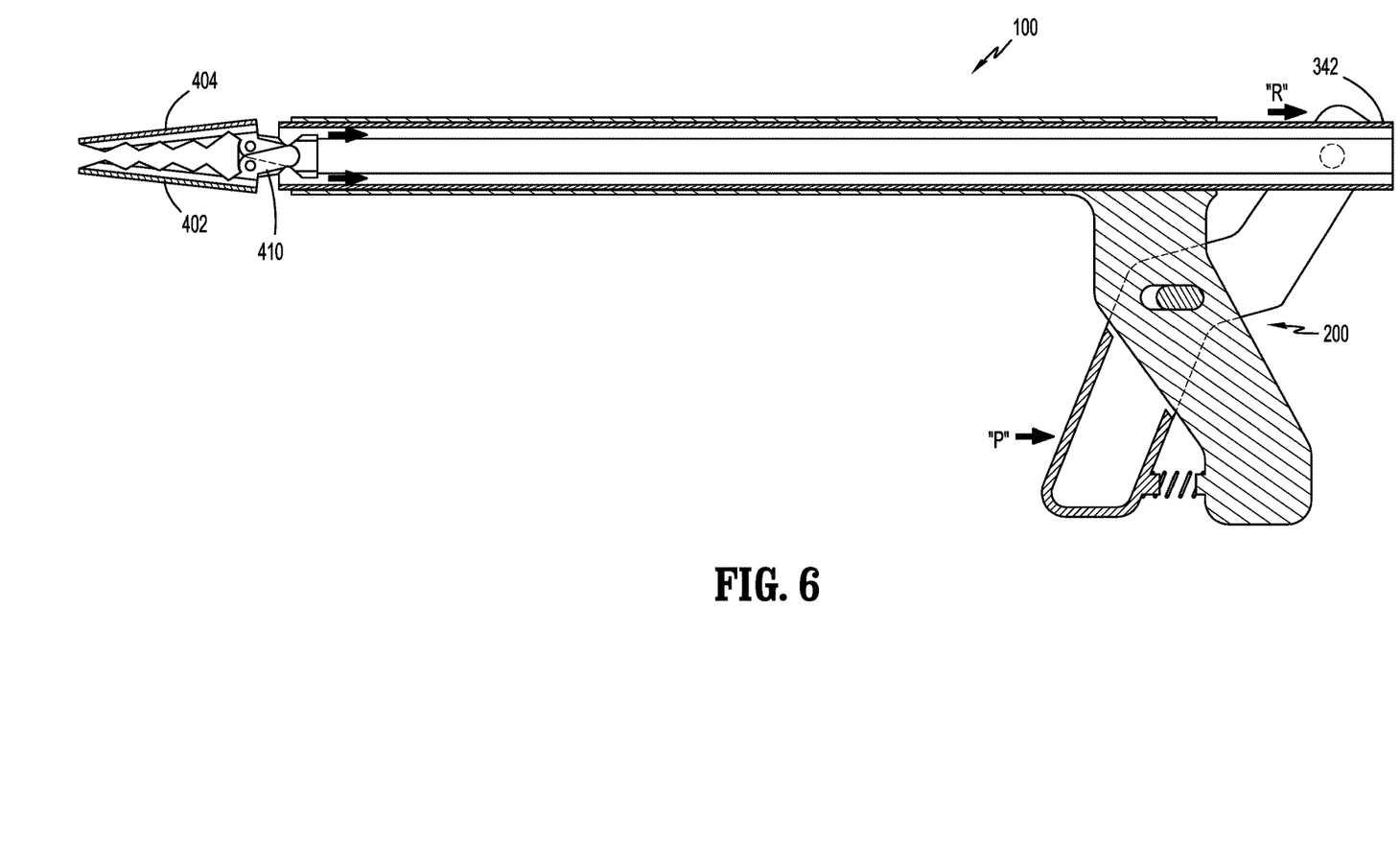
FIG. 6 is a side cross-sectional view of the surgical grasper of FIG. 3, illustrating approximation of jaws.

The inner shaft assembly 340 includes the inner shaft 342 defining an inner lumen 350 extending therethrough. The lumen 350 is dimensioned to receive surgical instruments therethrough. The inner shaft 342 is dimensioned to slidably extend through the first lumen 320 of the outer shaft 312. A proximal portion 340a of the inner shaft 342 includes bosses 346 (only one shown) that extend laterally outwards from an outer surface of the inner shaft 342. The bosses 346 are received in respective bores 246 of the second handle 240 of the handle assembly 200 and provide a pivotal connection. The second handle 240 further defines slots 244 to receive the camming pin 214 therein such that the camming pin 214 and the second handle 240 are movable as a single construct relative to the first handle 220. The second handle 240 further includes a boss 248 configured to support a second end of the spring 218 to bias the first and second handles 220, 240 away from each other. Under such a configuration, when the handle assembly 200 is squeezed by the clinician, the second handle 240 slides towards the first handle 220 in the direction of an arrow "P" (FIG. 6) and retracts the inner shaft 342 proximally in the direction of an arrow "R" (FIG. 6). The distal portion 340b of the inner shaft 342 includes an engaging portion 360 including teeth 362 that selectively engage the grasper assembly 400 to transition the grasper assembly 400 between the approximated and spaced apart configurations. In particular, the engaging portion 362 may include four teeth 362 that are spaced apart from adjacent teeth. For example, a first pair of teeth 362 may oppose a second pair of teeth 362. The teeth 362 are peripherally arranged and conform to the contour of the inner shaft 342 to maximize the space of the inner lumen 350. The inner lumen 350 may be structurally unobstructed and have a uniform diameter.

FIGS. 2 and 3 further illustrate the grasper 400 supported on the supporting fingers 330 of the outer shaft assembly 310. In particular, the grasper assembly 400 includes first and second jaws 402, 404. The first and second jaws 402, 404 are mirror images of each other. Each of the first and second jaws 402, 404 includes a grasping portion 406 including teeth 408 configured to grasp, e.g., tissue, and a pair of extension members 410. The pair of extension members 410 extends proximally from the grasping portion 406. The pair of extension members 410 defines a gap 410a dimensioned to receive the surgical instrument inserted through the inner lumen 350. In an aspect, the gap 410a may be equal to a diameter of the inner lumen 350. The extension members 410 may define an acute angle α with respect to a longitudinal axis "L-L" defined by the corresponding grasping portion 406. Each extension member 410 defines a bore 410b at or adjacent a distal portion 410c of the extension member 410. The bores 410b are dimensioned to receive the respective pins 334 extending through the bores 332 of the supporting fingers 330 of the outer shaft 312. Under such a configuration, the first and second jaws 402, 404 are pivotably supported on the supporting fingers 330. Portions of the extension members 410 are disposed proximal of the bores 332 of the supporting fingers 330. The portions of the extension members 410 disposed proximal of the bores 332 may selectively engage the engaging portion 360 of the inner shaft assembly 340 to transition the grasper assembly 400 between the approximated and spaced apart configurations, as will be described below.

Figure 4:
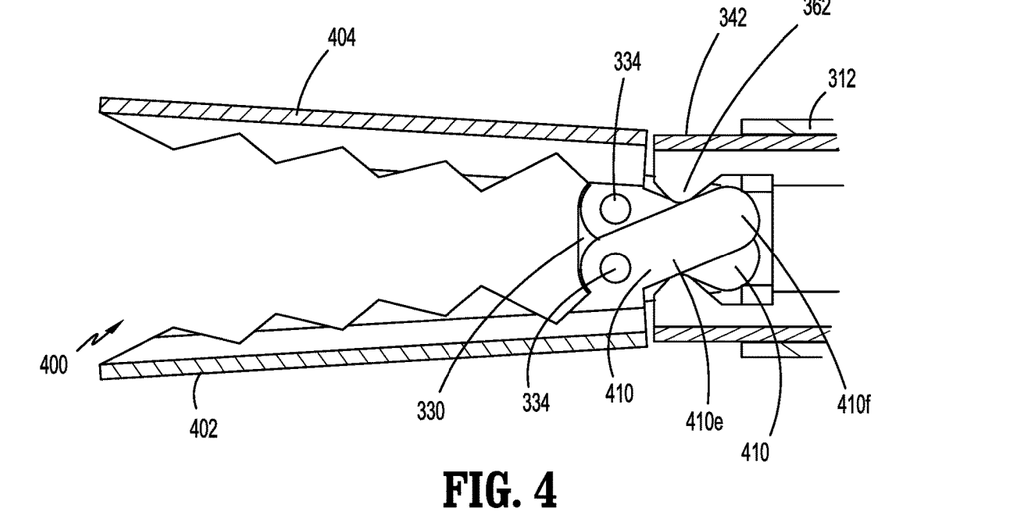
FIG. 4 is an enlarged view of the indicated area of detail of FIG. 3.
Figure 5:
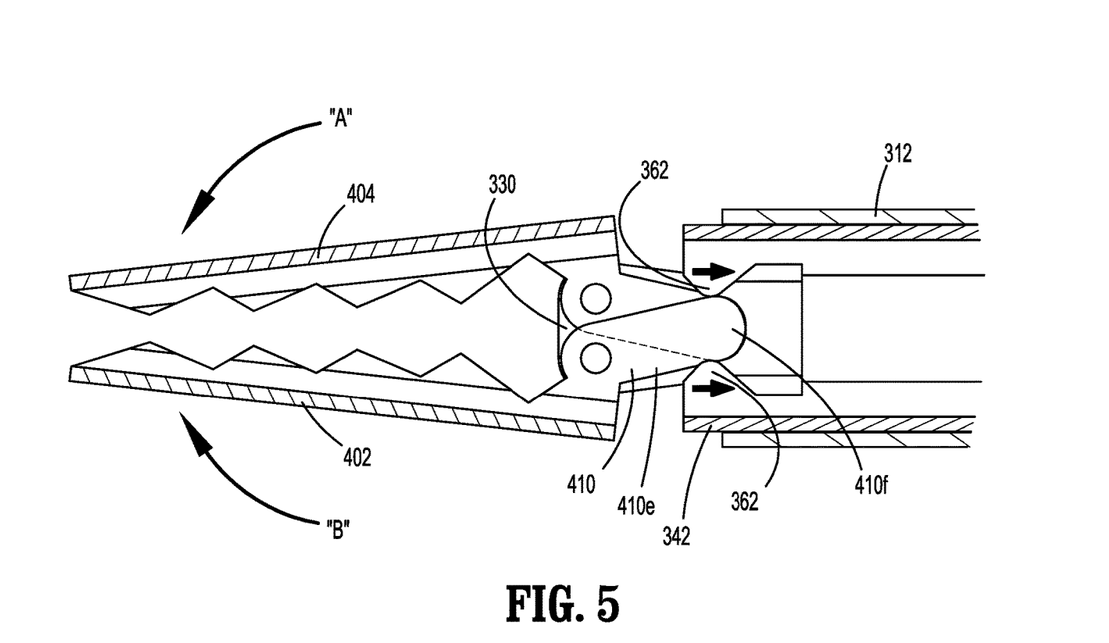
FIG. 5 is an enlarged view of the indicated area of detail of FIG. 3, illustrating approximation of jaws.

FIGS. 4 and 5 illustrate the grasping assembly 400 transitioning between the spaced apart and approximated configurations. The first and second jaws 402, 404 are pivotably coupled to the supporting fingers 330 such that when the inner shaft 342 is in a distal-most position (FIG. 4), the teeth 362 of the engaging portion 360 of the inner shaft assembly 340 engage respective central portions 410e of the extension members 410. In this manner, the first and second jaws 402, 404 are placed in the spaced apart configuration. When the inner shaft 342 is retracted to a proximal-most position (FIGS. 5 and 6), the teeth 362 of the engaging portion 360 of the inner shaft assembly 340 engage respective proximal portions 410f of the extension members 410. In this manner, the first and second jaws 402, 404 are placed in the approximated configuration (FIGS. 5 and 6).

Figures 7, 8:
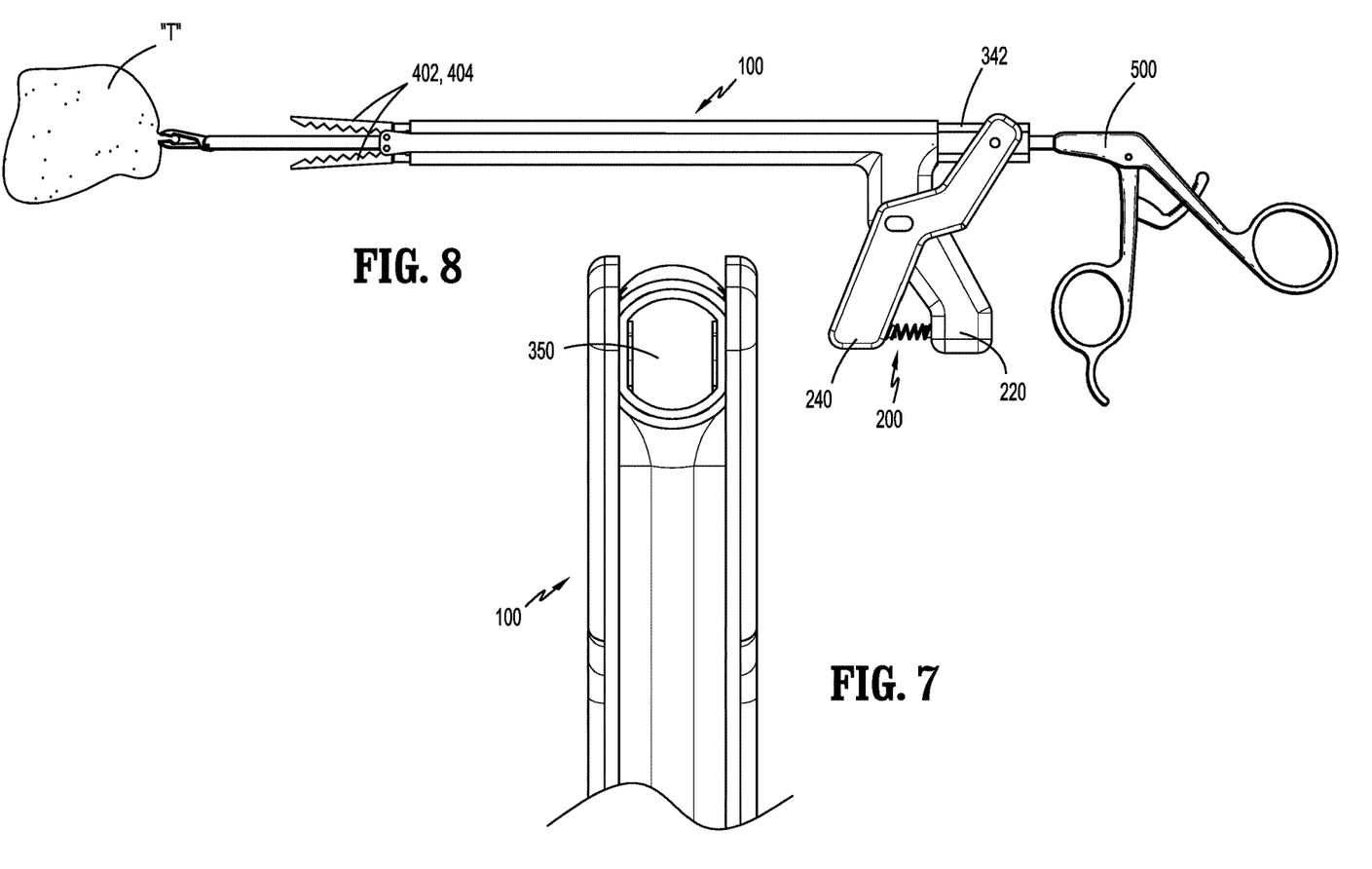
FIG. 7 is a partial rear end view of the surgical grasper of FIG. 1.
FIG. 8 is a side view of the surgical grasper of FIG. 1, illustrating use with a surgical instrument.
Figure 9:
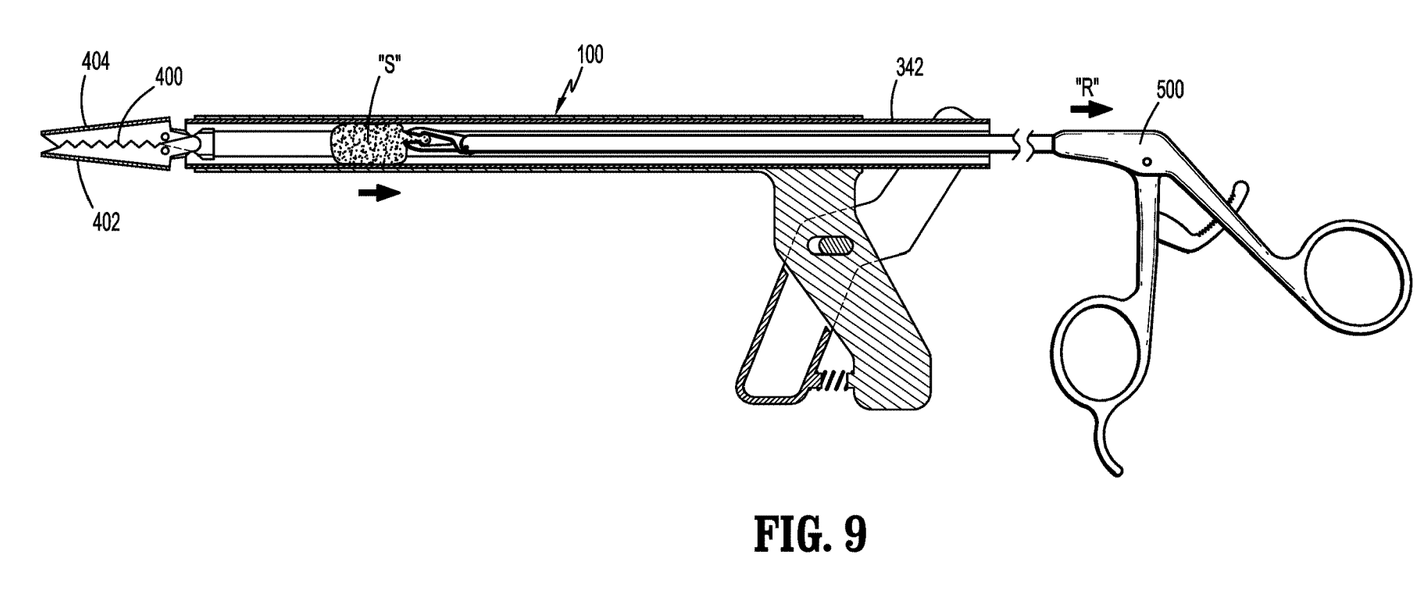
FIG. 9 is a side cut-away view of the surgical grasper of FIG. 1 with the surgical instrument partially inserted therein.

FIG. 7 illustrates the surgical grasper 100 defining the inner lumen 350 providing a passage to receive a surgical instrument therethrough. The surgical grasper 100 may be utilized with various surgical instruments. However, a second surgical grasper 500 is utilized for illustration purposes herein. In use, the surgical grasper 100 is inserted through an opening in tissue and may be manipulated as needed to be placed adjacent a surgical site. For example, the handle assembly 200 may be actuated to remove tissue "T". Specifically, as the first and second handles 220, 240 are squeezed together, the inner shaft 342 is retracted in the direction of the arrow "R". At this time, the first and second jaws 402, 404 may sever and grasp tissue "T". Tissue "T" may be retained by the first and second jaws 402, 404. At this time, the second surgical grasper 500 may be inserted through the inner lumen 350 (FIG. 7) of the surgical grasper 100 and retrieve tissue specimen "S" severed by the first and second jaws 402, 404 (FIGS. 8 and 9). By allowing the second surgical grasper 500 to be inserted through the surgical grasper 100, the invasiveness (i.e., the number of incisions) of the surgical procedure is minimized and the risk of contamination of the surgical site by the tissue specimen "S" is also reduced.

Figure 10:
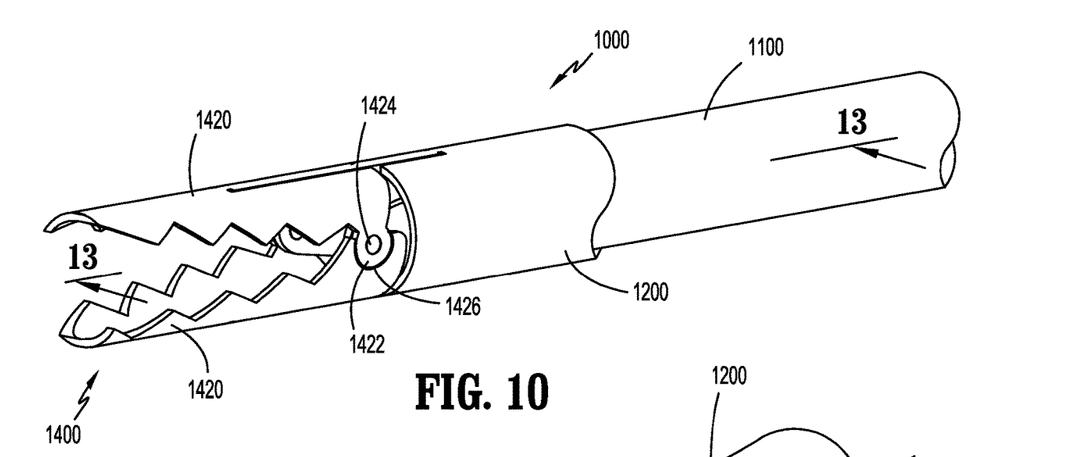
FIG. 10 is a partial perspective view of a surgical grasper in accordance with another aspect of the disclosure.
Figure 11:
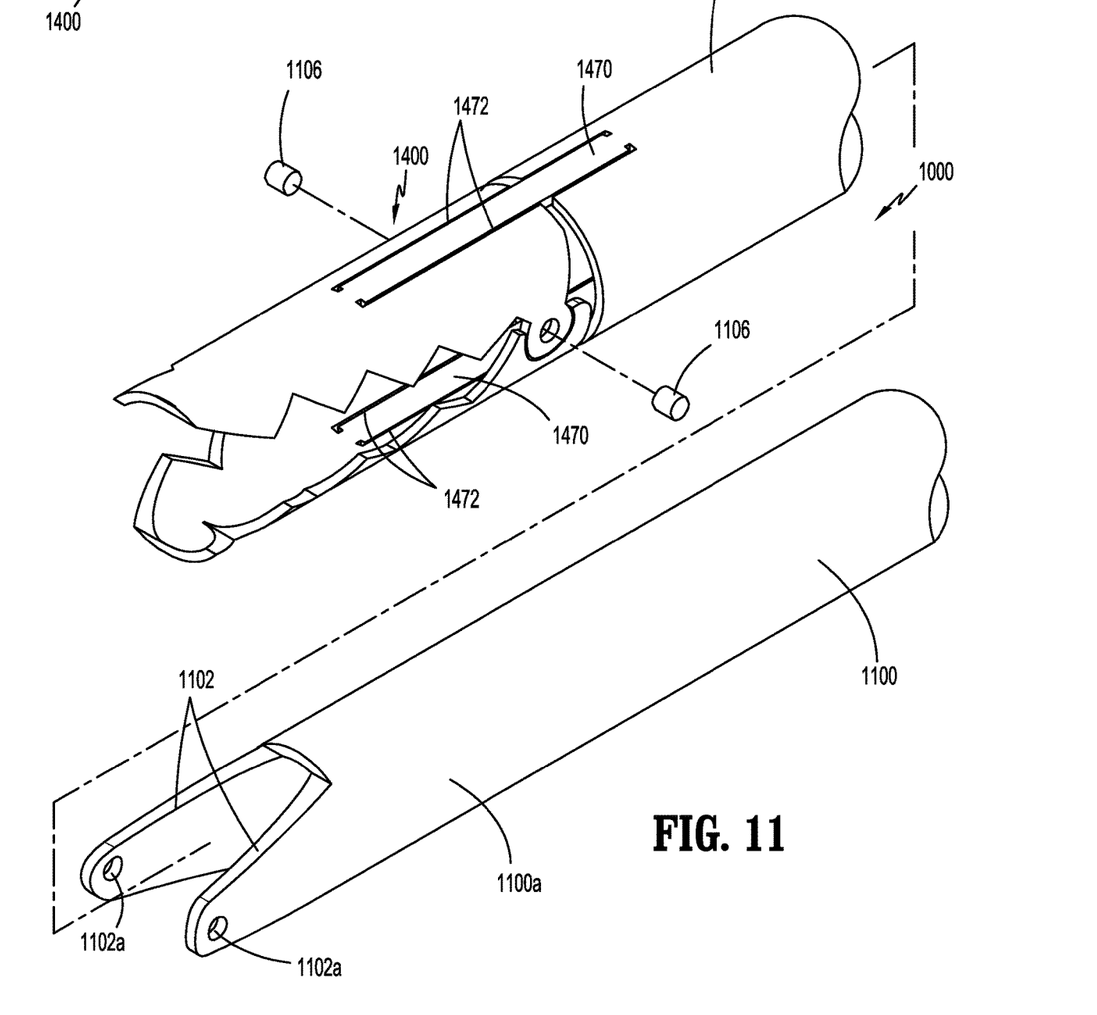
FIG. 11 is an exploded perspective view of the surgical grasper of FIG. 10.
Figure 12:
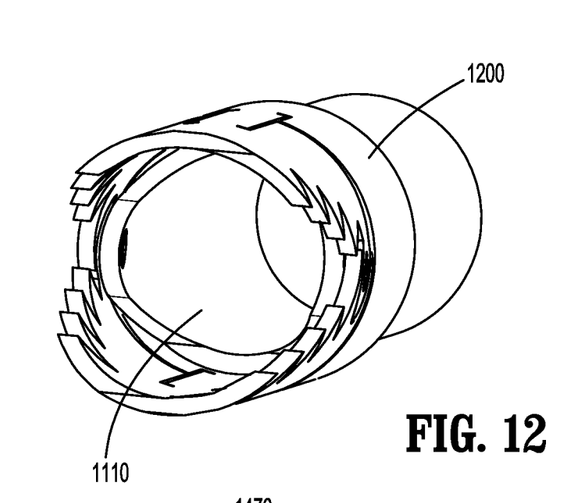
FIG. 12 is a front perspective view of the surgical grasper of FIG. 13.

FIGS. 10 and 11 illustrate a surgical grasper 1000 in accordance with another aspect of the disclosure. In particular, the surgical grasper 1000 has a grasper assembly 1400 formed from a single tubular member, thereby reducing the cost of manufacture. The surgical grasper 1000 includes an inner shaft 1100 and an outer shaft 1200. The inner shaft 1100 is slidably received in the outer shaft 1200. The inner shaft 1100 defines an inner lumen 1110 (FIG. 15) dimensioned to receive surgical instruments therethrough. The inner shaft 1100 includes as a distal portion 1100a having laterally opposing fingers 1102. Each finger 1102 defines a bore 1102a dimensioned to receive a pin 1106 to pivotably couple the grasper assembly 1400 thereto, as will be discussed. The outer shaft 1200 and the grasper assembly 1400 are formed from a single tubular member. The outer shaft 1200 defines a lumen dimensioned to receive the inner shaft 1100. The single tubular member is cut to include jaws 1420. The jaws 1420 may be identical. Each jaw 1420 includes an arcuate portion 1422 defining a bore 1424, and a recess 1426 having a shape complementary to a shape of the arcuate portion 1422 of the other jaw 1420. Under such a configuration, the jaws 1420 may be transitionable between approximated and spaced apart configurations. The single tubular member is also cut to provide diametrically opposing connectors 1470 to connect respective jaws 1420 to the outer shaft 1200. In particular, the single tubular member further defines axial slots 1472 to enable flexing of the connectors 1470.

Figure 13:
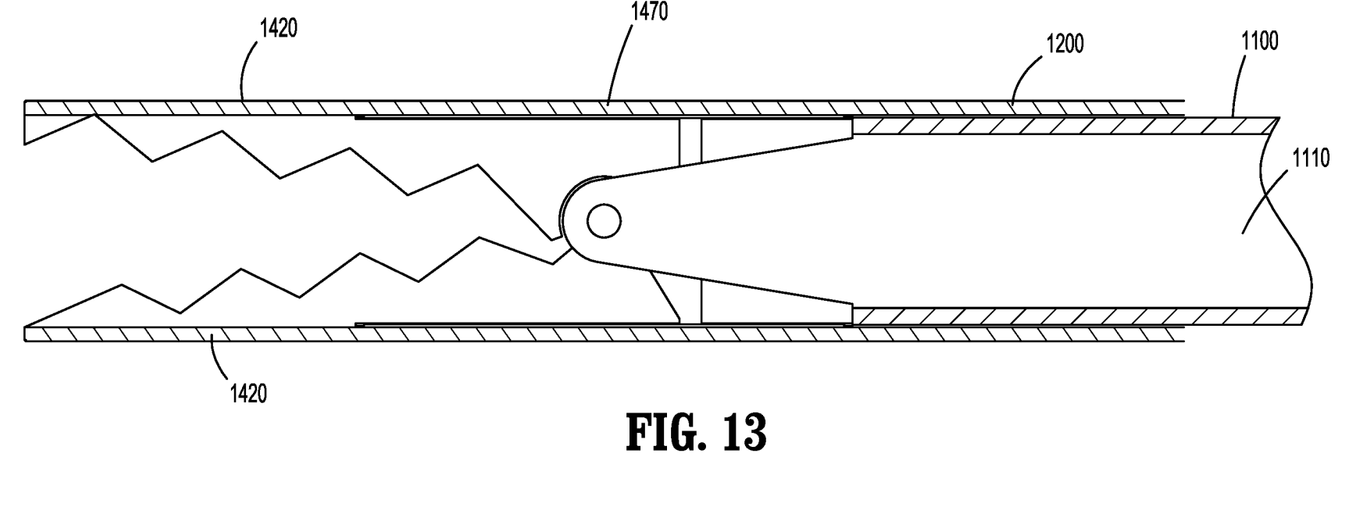
FIG. 13 is a side cross-sectional view of the surgical grasper of FIG. 10 taken along section line 13-13 of FIG. 10.
Figure 14:
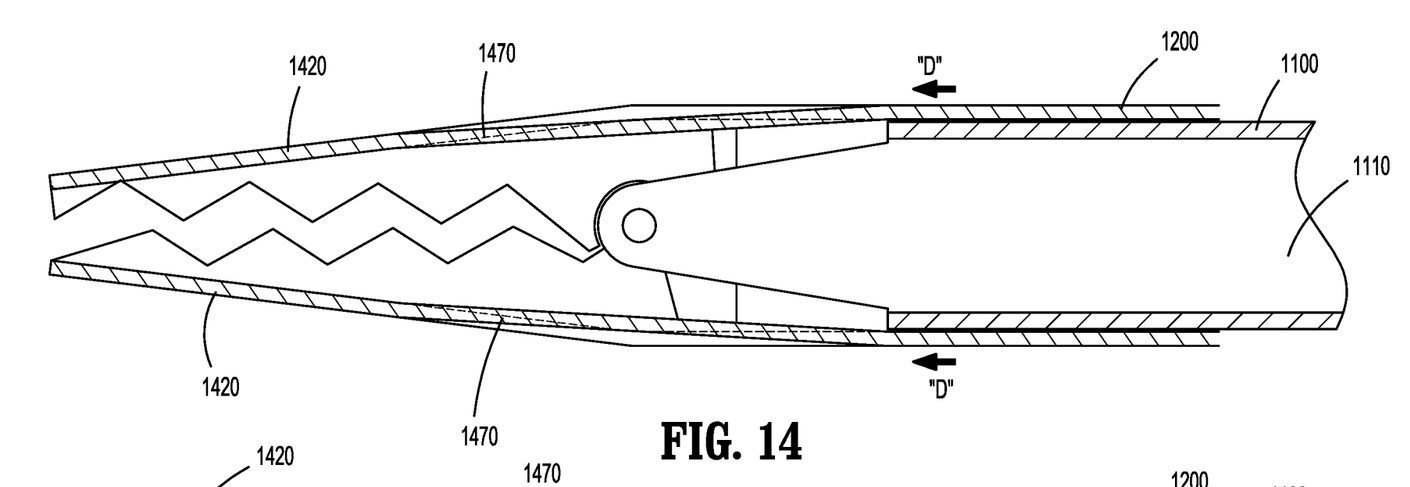
FIG. 14 is a side cross-sectional view of the surgical grasper of FIG. 12, illustrating approximation of jaws.
Figure 15:
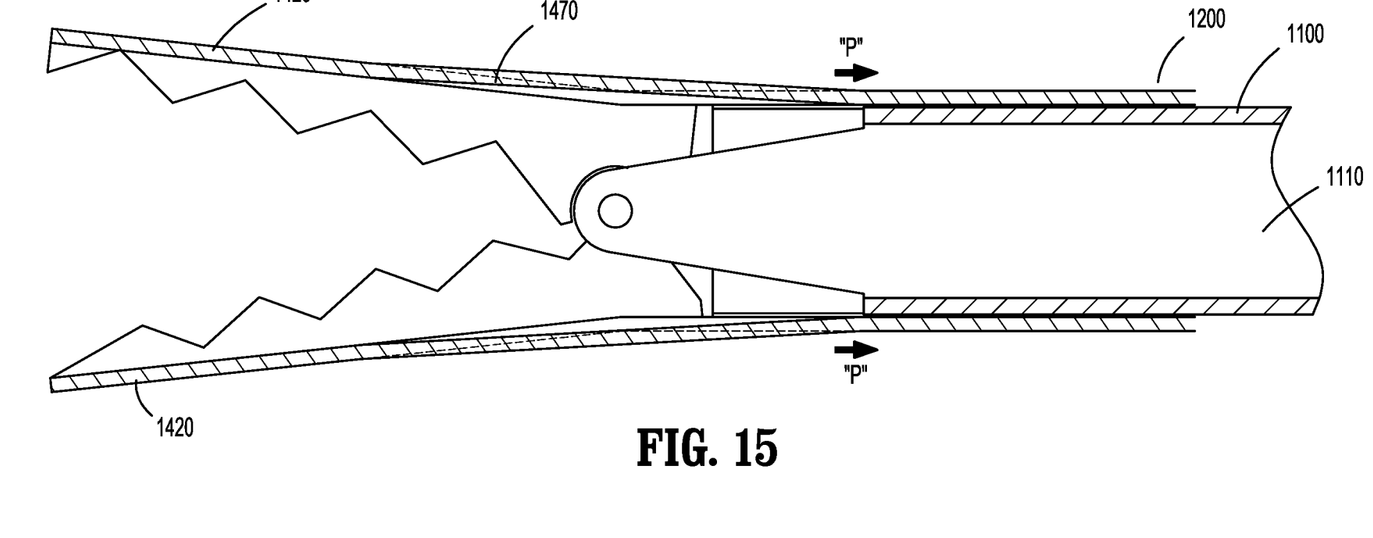
FIG. 15 is a side cross-sectional view of the surgical grasper of FIG. 13, illustrating opening of the jaws.

Under such a configuration, the pins 1106 couple the jaws 1420 to the inner shaft 1100 to enable rotation of the jaws 1420. Further, the connectors 1470 are configured to flex to enable transitioning of the jaws 1420 between the approximated and spaced apart configurations. FIG. 13 illustrates the inner shaft 1100 in a neutral position. At this time, the jaws 1420 and the connectors 1470 are aligned with the outer shaft 1200. FIG. 14 illustrates the inner shaft 1100 in a distal-most position. At this time, the axial displacement of the inner shaft 1100 in the direction of an arrow "D" causes the connectors 1470 (shown in phantom) to flex radially outwards such that the jaws 1420 are transitioned to the approximated configuration. FIG. 15 illustrates the inner shaft 1100 in a proximal-most position. At this time, the axial displacement of the inner shaft 100 in the direction of an arrow "P" causes the connectors 1470 (shown in phantom) to flex radially inwards such that the jaws 1420 are transitioned to the spaced apart configuration. The method of use of the surgical grasper 1000 is substantially identical to the method of use of the surgical grasper 100 described hereinabove, and thus will not be described herein.

It is also envisioned that the surgical graspers 100, 1000 may be adapted for use with a robotic surgical system. For example, the robotic surgical system may activate the handle assembly 200. It is also contemplated that the handle assembly 200 may further include a locking mechanism configured to selectively lock the relative position of the first and second handles 220, 240. It is further contemplated that the surgical graspers 100, 1000 may include a seal assembly to maintain, e.g., insufflation fluids, within the body cavity during surgery.

While various configurations have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A surgical grasper comprising:
   a handle assembly including a first handle and a second handle;
   an inner shaft assembly including an inner shaft defining a lumen for passage of a surgical instrument and an engaging portion peripherally arranged with a distal portion of the inner shaft such that the engaging portion conforms to a contour of the inner shaft, a proximal portion of the inner shaft pivotably coupled to the first handle;
   an outer shaft slidably disposed about the inner shaft, the outer shaft including a proximal portion fixedly secured to the second handle, and a distal portion including supporting fingers, each of the supporting fingers defining apertures; and
   a grasper assembly operatively coupled to the supporting fingers of the outer shaft, the grasper assembly including a first jaw and a second jaw, the first jaw including a first grasping portion and a first pair of extension members extending proximally from the first grasping portion such that the first pair of extension members selectively engage the engaging portion of the inner shaft assembly, the second jaw including a second grasping portion and a second pair of extension members extending proximally from the second grasping portion such that the second pair of extension members selectively engage the engaging portion of the inner shaft assembly, wherein the first pair of extension members and the second pair of extension members each define bores, the bores of the first and second pair of extension members dimensioned to receive pins extending through the apertures of the supporting fingers such that axial displacement of the inner shaft transitions the grasper assembly between an approximated configuration and a spaced apart configuration.

2. The surgical grasper according to claim 1, wherein when the inner shaft is in a distal-most position, the engaging portion of the inner shaft assembly engages central portions of the first pair of extension members and the second pair of extension members of the grasper assembly to transition the grasper assembly to the spaced apart configuration.

3. The surgical grasper according to claim 1, wherein when the inner shaft is in a proximal-most position, the engaging portion of the inner shaft assembly engages proximal end portions of the first pair of extension members and the second pair of extension members of the grasper assembly to transition the grasper assembly to the approximated configuration.

4. The surgical grasper according to claim 1, wherein the supporting fingers of the outer shaft extend distally from an outer surface of the outer shaft.

5. The surgical grasper according to claim 1, wherein at least one of the first pair of extension members or the second pair of extension members defines an acute angle with respect to a longitudinal axis defined by the corresponding grasping portion of the grasper assembly.

6. The surgical grasper according to claim 1, wherein the engaging portion of the inner shaft assembly includes teeth to engage the first pair of extension members or the second pair of extension members.

7. The surgical grasper according to claim 1, wherein the first handle and the second handle of the handle assembly are biased away from each other.

8. The surgical grasper according to claim 1, wherein the first handle is axially movable relative to the second handle.

9. The surgical grasper according to claim 1, wherein the first pair of extension members defines a first gap and the second pair of extension members defines a second gap.

10. The surgical grasper according to claim 9, wherein the first gap or the second is substantially identical to a diameter of the lumen defined by the inner shaft.

11. The surgical grasper according to claim 1, wherein the first pair of extension members pivot about a first axis and the second pair of extension members pivot about a second axis different from the first axis.

12. A surgical grasper comprising:
    an inner shaft assembly including an inner shaft defining a lumen for passage of a surgical instrument and an engaging portion peripherally arranged with the inner shaft such that the engaging portion conforms to a contour of the inner shaft;
    an outer shaft slidably disposed about the inner shaft, the outer shaft including opposing supporting fingers, each of the supporting fingers including apertures;
    a grasper assembly operatively coupled to the opposing supporting fingers of the outer shaft, the grasper assembly including a first jaw and a second jaw, the first jaw including a first grasping portion and a first pair of extension members extending proximally from the first grasping portion such that the first pair of extension members selectively engages the inner shaft, the second jaw including a second grasping portion and a second pair of extension members extending proximally from the second grasping portion such that the second pair of extension members selectively engages the inner shaft, the first pair of extension members and the second pair of extension members including bores, wherein axial displacement of the inner shaft transitions the grasper assembly between an approximated configuration and a spaced apart configuration; and
    pins extending through each of the bores of the first pair of extension members, each of the bores of the second pair of extension members, and each of the apertures of the supporting fingers thereby coupling the first pair of extension members, the second pair of extension members, and the supporting fingers.

13. The surgical grasper according to claim 12, wherein the outer shaft defines a lumen to receive the inner shaft.

14. The surgical grasper according to claim 12, wherein the lumen of the inner shaft has a uniform diameter.

15. The surgical grasper according to claim 12, wherein each extension member of the first and second pair of extension members has a thickness smaller than or equal to a thickness of the outer shaft.

16. The surgical grasper according to claim 12, wherein the first pair of extension members pivots about a first axis and the second pair of extension member pivots about a second axis different from the first axis.

17. A surgical grasper comprising:

a first handle;

a second handle pivotably coupled to the first handle;

an outer shaft coupled to the first handle, the outer shaft including fingers extending from a distal end of the outer shaft, each of the fingers including apertures;

an inner shaft slidably disposed in the outer shaft and operably coupled to the first handle, the inner shaft having teeth disposed at a distal end of the inner shaft; and a grasping assembly having a first jaw and a second jaw, the first jaw and the second jaw pivotably coupled to the fingers of the outer shaft such that the first jaw and the second jaw are transitionable between an approximated configuration and a spaced apart configuration, the first jaw having a first pair of extensions and the second jaw having a second pair of extensions, the first pair of extensions and the second pair of extensions operably engaged with the teeth of the inner shaft such that axial movement of the inner shaft relative to the outer shaft transitions the first jaw and the second jaw between the approximated configuration and the spaced apart configuration, the first pair of extensions and the second pair of extensions each define bores that are dimensioned to receive pins extending through the apertures of the fingers thereby operably coupling the first pair of extensions and the second pair of extensions to the fingers.

18. The surgical grasper according to claim 17, wherein when the inner shaft is in a distal position relative to the outer shaft, the teeth of the inner shaft engage central portions of the first pair of extensions and the second pair of extensions thereby defining the spaced apart configuration of the first jaw and the second jaw.

19. The surgical grasper according to claim 17, wherein when the inner shaft is in a proximal position relative to the outer shaft, the teeth of the inner shaft engage proximal ends of the first pair of extensions and the second pair of extensions thereby defining the approximated configuration of the first jaw and the second jaw.

20. The surgical grasper according to claim 17, wherein the first pair of extensions pivots about a first axis and the second pair of extensions pivots about a second axis different from the first axis.

* * * * *